United States Patent
Stoller et al.

(10) Patent No.: US 10,820,476 B2
(45) Date of Patent: Nov. 3, 2020

(54) APPARATUS, SYSTEM AND METHOD FOR MONITORING SOIL CRITERIA DURING TILLAGE OPERATIONS AND CONTROL OF TILLAGE TOOLS

(71) Applicant: Precision Planting LLC, Tremont, IL (US)

(72) Inventors: Jason Stoller, Eureka, IL (US); Justin McMenamy, Edwards, IL (US); Matthew Morgan, Peoria, IL (US); Dale Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 387 days.

(21) Appl. No.: 15/924,267

(22) Filed: Mar. 18, 2018

(65) Prior Publication Data
US 2018/0206393 A1    Jul. 26, 2018

Related U.S. Application Data

(63) Continuation of application No. PCT/US2016/052285, filed on Sep. 16, 2016.
(Continued)

(51) Int. Cl.
| | |
|---|---|
| *A01B 79/00* | (2006.01) |
| *A01B 63/32* | (2006.01) |
| *A01B 15/00* | (2006.01) |
| *A01B 49/06* | (2006.01) |
| *G01S 13/88* | (2006.01) |
| *A01B 33/16* | (2006.01) |

(Continued)

(52) U.S. Cl.
CPC ............ *A01B 79/005* (2013.01); *A01B 33/16* (2013.01); *A01B 35/32* (2013.01); *A01B 49/06* (2013.01); *A01B 63/008* (2013.01); *A01B 63/24* (2013.01); *A01B 76/00* (2013.01); *A01C 21/005* (2013.01); *G01N 33/24* (2013.01); *G01S 13/885* (2013.01); *A01B 21/08* (2013.01); *A01B 49/027* (2013.01); *A01B 63/111* (2013.01); *A01B 63/32* (2013.01); *G01N 2033/245* (2013.01)

(58) Field of Classification Search
None
See application file for complete search history.

(56) References Cited

U.S. PATENT DOCUMENTS

| | | |
|---|---|---|
| 4,703,810 A | 11/1987 | Meiners |
| 5,161,622 A | 11/1992 | Godbersen |

(Continued)

FOREIGN PATENT DOCUMENTS

| | | |
|---|---|---|
| EP | 2267566 A3 | 12/2014 |
| JP | 08056401 A | 3/1996 |

(Continued)

OTHER PUBLICATIONS

International Search Report and Written Opinion, PCT Application No. PCT/US2016/052285, dated Nov. 18, 2016, 19 pages.

*Primary Examiner* — Adam D Tissot

(57) ABSTRACT

A tillage implement comprising a frame operably supporting tillage tools, and a soil monitoring system comprising instrumentation operably supported from the frame and disposed to detect soil criteria before, after, or before and after the soil is tilled by the tillage tools. The soil criteria detected is at least one of surface residue criteria, soil clod size criteria and soil shatter criteria.

37 Claims, 5 Drawing Sheets

Related U.S. Application Data

(60) Provisional application No. 62/220,896, filed on Sep. 18, 2015.

(51) Int. Cl.

| | | |
|---|---|---|
| *A01B 35/32* | (2006.01) |
| *A01B 63/00* | (2006.01) |
| *A01B 63/24* | (2006.01) |
| *A01B 76/00* | (2006.01) |
| *A01C 21/00* | (2006.01) |
| *G01N 33/24* | (2006.01) |
| *A01B 63/111* | (2006.01) |
| *A01B 21/08* | (2006.01) |
| *A01B 49/02* | (2006.01) |

(56) References Cited

U.S. PATENT DOCUMENTS

| | | | |
|---|---|---|---|
| 5,462,123 A | 10/1995 | Harlan et al. | |
| 5,841,282 A | 11/1998 | Christy et al. | |
| 6,041,582 A | 3/2000 | Tiede et al. | |
| 6,452,177 B1 | 9/2002 | Feldman et al. | |
| 6,484,652 B1 * | 11/2002 | Colburn, Jr. | A01B 79/005 |
| | | | 111/118 |
| 6,497,153 B1 | 12/2002 | Hoskinson et al. | |
| 8,544,398 B2 | 10/2013 | Bassett | |
| 8,673,713 B2 | 7/2014 | Bassett | |
| 9,585,301 B1 * | 3/2017 | Lund | A01B 49/04 |
| 2003/0066357 A1 | 4/2003 | Upadhyaya et al. | |
| 2005/0005704 A1 | 1/2005 | Adamchuk et al. | |
| 2009/0288820 A1 | 11/2009 | Barron et al. | |
| 2011/0126746 A1 * | 6/2011 | Borland | A01C 5/04 |
| | | | 111/149 |
| 2012/0089304 A1 | 4/2012 | Hamilton et al. | |
| 2012/0125244 A1 | 5/2012 | Beaujot | |
| 2012/0201415 A1 * | 8/2012 | Bredehoft | G06K 9/00657 |
| | | | 382/100 |
| 2013/0046419 A1 | 2/2013 | Anderson et al. | |
| 2013/0143191 A1 | 6/2013 | Zemenchik et al. | |
| 2013/0180742 A1 * | 7/2013 | Wendte | A01B 63/1145 |
| | | | 172/4 |
| 2014/0026748 A1 | 1/2014 | Stoller et al. | |
| 2014/0041563 A1 | 2/2014 | Henry et al. | |
| 2014/0067209 A1 | 3/2014 | Casper et al. | |
| 2014/0116735 A1 * | 5/2014 | Bassett | A01C 5/06 |
| | | | 172/2 |
| 2014/0236431 A1 | 8/2014 | Hendrickson et al. | |
| 2014/0290545 A1 | 10/2014 | Van Buskirk et al. | |
| 2014/0303854 A1 | 10/2014 | Zielke | |
| 2016/0029547 A1 | 2/2016 | Casper et al. | |
| 2019/0141880 A1 * | 5/2019 | Zemenchik | A01B 63/32 |
| | | | 172/1 |

FOREIGN PATENT DOCUMENTS

| | | |
|---|---|---|
| JP | 08289610 A | 11/1996 |
| JP | 10304712 A | 11/1998 |
| JP | 11275911 A | 10/1999 |
| JP | 2007000087 A | 1/2007 |
| JP | 2008211971 A | 9/2008 |
| JP | 2015188427 A | 11/2015 |
| JP | 2015188428 A | 11/2015 |
| WO | 0249414 A1 | 9/2002 |
| WO | 2012102667 A1 | 8/2012 |

* cited by examiner

APPARATUS, SYSTEM AND METHOD FOR MONITORING SOIL CRITERIA DURING TILLAGE OPERATIONS AND CONTROL OF TILLAGE TOOLS

BACKGROUND

Seed bed preparation is critical for proper seed germination and plant growth. Too much crop residue within or covering the seed furrow can adversely affect seed germination and interfere with plant growth. Additionally, seed germination and plant growth can be adversely affected if the seed bed includes large surface clods and soil density changes due to compaction layers within the root zone. Accordingly, there is a need for an apparatus, system and method which is capable of monitoring soil characteristics or criteria during tillage operations so as to make adjustments to the tillage implement and other implements while on-the-go to improve soil conditions and seed bed preparation.

DESCRIPTION

Deep tillage is the practice of performing tillage operations at depths of more than twelve inches designed to shatter the compacted soil at that depth. Examples of a deep tillage implements include the implement disclosed in U.S. Pat. No. 4,703,810 and in commercially available implements such as the Case IH 870 Chisel Plow/Ripper, as well as other makes and models of commercially available deep tillage implements recognized by those of skill in the art.

Shallow tillage is used to condition the seed bed and incorporate nutrients at soil depths typically between two to six inches in depth. Examples of shallow tillage implements include field cultivators, an example of which is disclosed in U.S. Pat. No. 5,161,622 and in commercially available field cultivators such as the Case IH Tiger-Mate® 200 and as well as other makes and models of commercially available field cultivators recognized by those of skill in the art. Other shallow tillage implements may include a disk harrow, such as the Case IH Tru-Tandem™ 345 disk harrow and other makes and models of commercially available disk harrows recognized by those of skill in the art. Still other types of shallow tillage implements include soil finishers such as spike harrows, tine harrows, rolling basket harrows, etc., as recognized by those of skill in the art.

Figure 1:
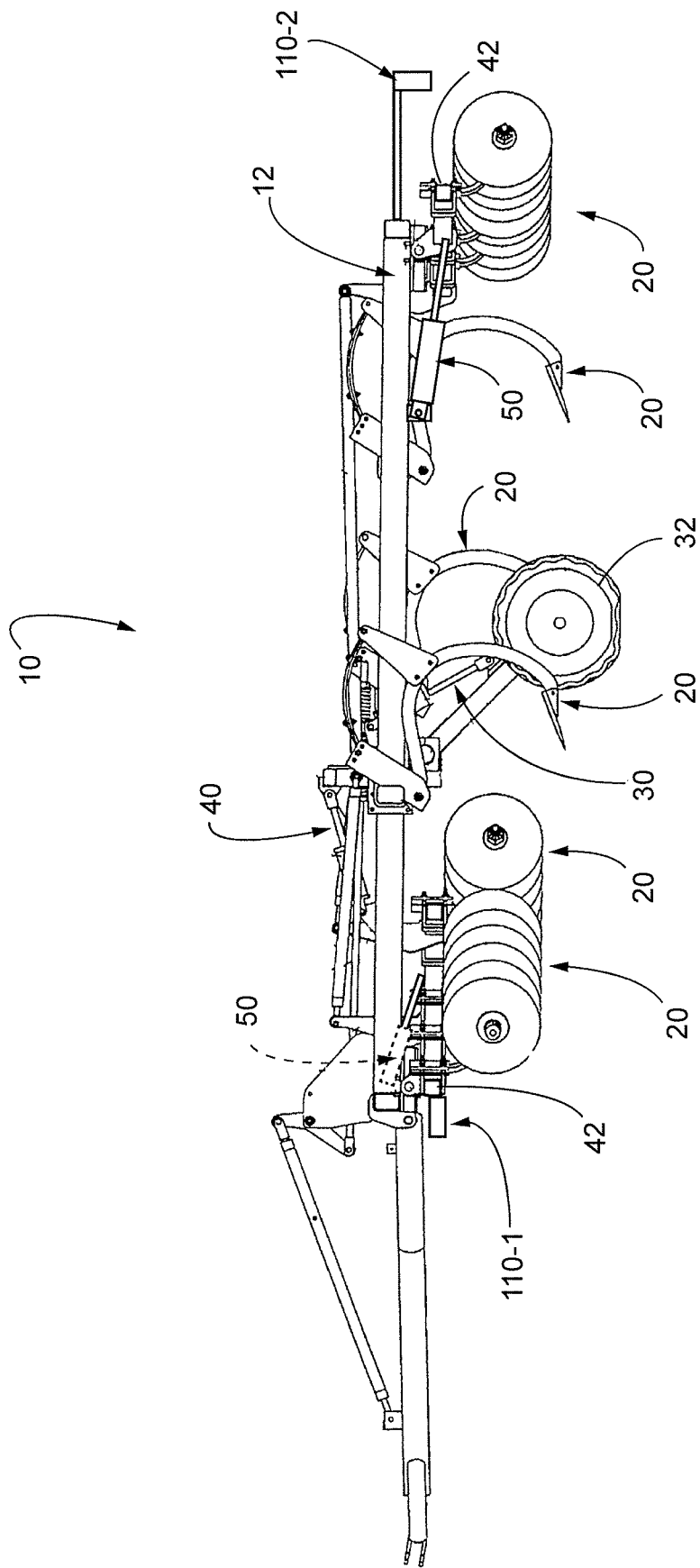
FIG. 1 is a side elevation view of an embodiment of a tillage implement.
Figure 2:
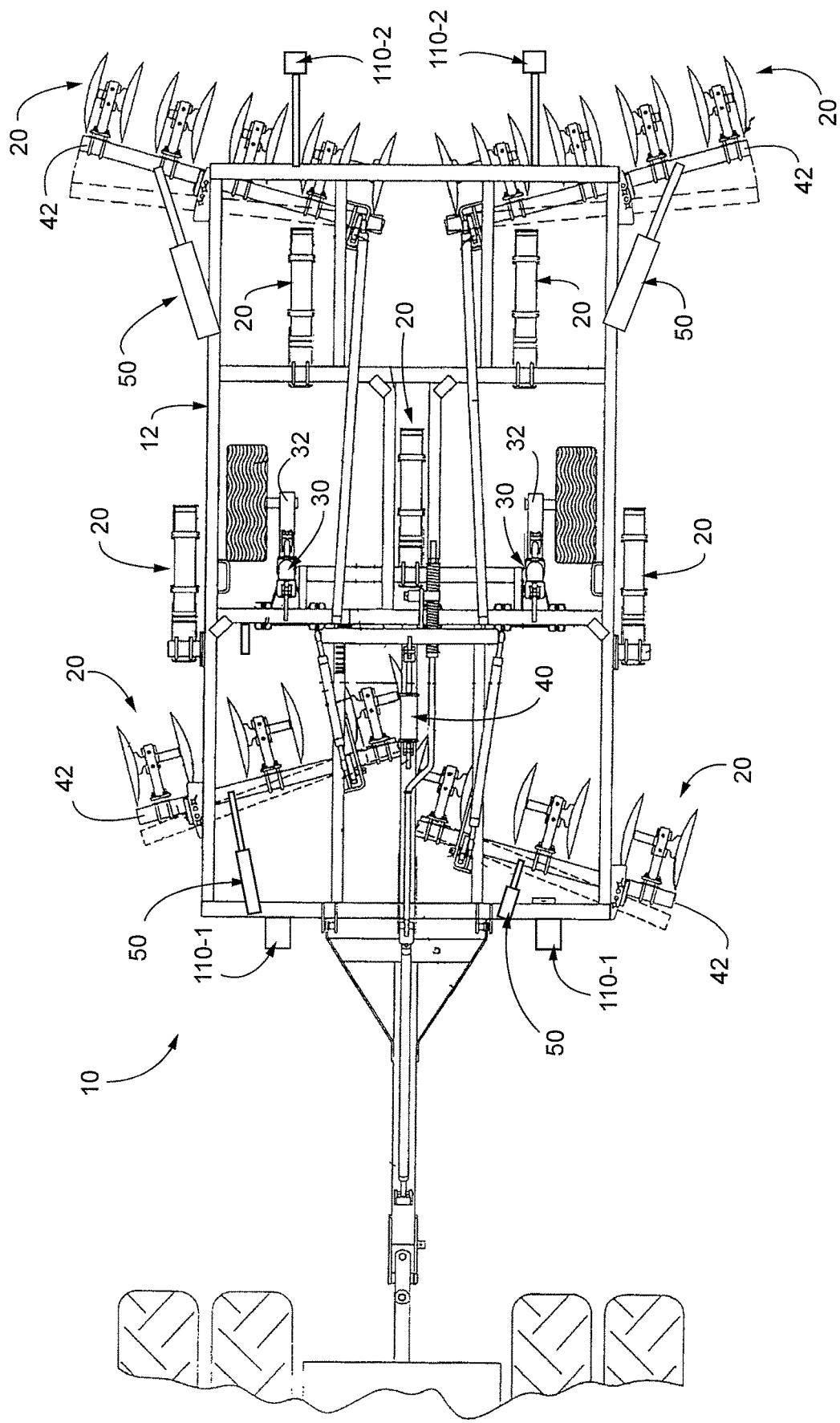
FIG. 2 is a top plan view of the tillage implement of FIG. 1.

Both deep tillage implements and shallow tillage implements are generally referred to herein as "tillage implements" 10. FIG. 1 is a side elevation view illustrating an example of a tillage implement 10. FIG. 2 is a top plan view of the tillage implement 10 of FIG. 1. Regardless of the type of the type of implement, i.e., ripper, field cultivator, disk harrow, soil finisher, etc., the tillage implement 10 generally comprises a main frame 12 which attaches to a drawbar of a tractor 14. The main frame 12 operatively supports a plurality of tillage tools 20. Depending on the type of tillage implement 10, the tillage tools 20 may comprise shanks, or tines with sweeps or points, discs gangs, rolling baskets, spike, coil tines or any other type of tillage tool as recognized by those of skill in the art. As is well known in the art, the main frame 12 includes a height adjustment actuator 30 coupled to a wheel assembly 32 for raising or lowering the wheel assembly 32 with respect to the main frame 12 to adjust the working depth of the tillage tools 20 and for raising the tillage tools 20 above the ground for over-the-road travel. Additionally, the tillage implement 10 may include separate tool depth adjustment actuators 40 and related assembly system coupled to subframes 42 supporting gangs of tillage tools (e.g., a disc gang) so as to lower the subframe 42 with respect to the main frame 12 to increase the depth of penetration of only those tillage tools supported by the subframe 42. An example of a tillage implement 10 with a tool depth adjustment actuator 40 and related assembly system is disclosed in U.S. Pat. No. 5,462,123, incorporated herein by reference. Additionally, the tillage implement 10 may include an angular adjustment actuator 50 and related assembly systems coupled between the main frame 12 and subframes 42 for adjusting the angle of the subframe 42 with respect to the main frame 12 and the direction of travel of the tillage implement 10. An example of a tillage implement 10 with an angle adjustment actuator 50 and related assembly system is disclosed in U.S. Pat. No. 5,161,622, incorporated herein by reference. Additionally, the tillage implement 10 may include a down force adjustment actuator 60 (FIG. 3) and related assembly systems coupled between the main frame 12 and subframes 42 for adjusting the down force or down pressure exerted by the tillage tools 20, such as, for example, a rolling basket.

Figure 3:
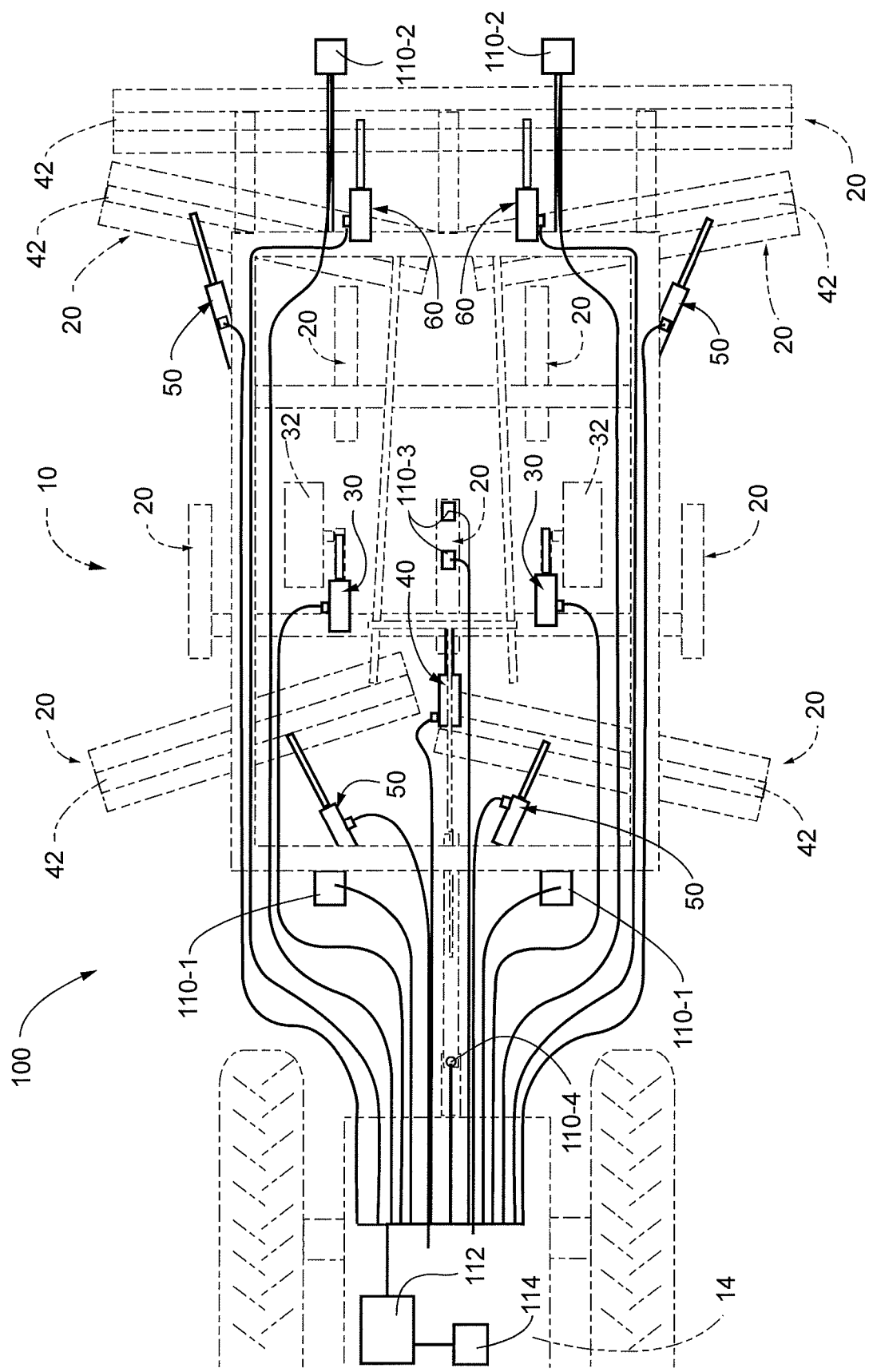
FIG. 3 is schematic illustration of an embodiment of a soil monitoring apparatus on an embodiment of a tillage implement.

The tillage implement 10 is instrumented with a soil monitoring system 100 (FIG. 3) to monitor certain soil criteria 200 of the soil that has just been tilled. The instrumentation 110 comprising the soil monitoring system 100 may be mounted onto the tillage implement 10 behind the tillage tools 20 to only monitor the soil after it is tilled, before it is tilled, or, alternatively, as shown in FIG. 3, the soil monitoring system 100 may include both fore and aft instrumentation 110-1, 110-2 to detect or measure the soil criteria 200 ahead of the tillage implement 10 and after the tillage implement 10 to provide a before-and-after comparison of the soil criteria 200 thereby detecting or measuring the effect of the tillage implement 10, such as a percentage difference of the soil criteria 200. The soil monitoring system 100 includes a display monitor 112 mounted in the cab of the tractor 14. The instrumentation 110 is electrically coupled to the display monitor 112 to communicate output signals generated by the instrumentation 110 to the display monitor 112 which visually displays the measured or detected soil criteria 200 to the operator live or in real-time. The display monitor 112 interfaces with a global positioning system 114 and includes a user interface, such as a graphical user interface (GUI) and memory for storing the data comprising the soil criteria 200 in relation to the GPS coordinates for mapping the soil criteria 200 throughout the field. The display monitor 112 may also be electrically coupled to the height adjustment actuators 30, the tool depth adjustment actuators 40, the angular adjustment actuators 50 and the downforce actuators 60, for automatic actuation as described below. It should be appreciated that for automatic actuation, the actuators 30, 40, 50, 60 would be coupled to solenoid valves to receive signal generated by the display monitor 112 in response to signals produced by the instrumentation 110 measuring or detecting the soil criteria 200. The solenoid valves control the flow of hydraulic fluid to the actuators 30, 40, 50, 60 to extend and retract the actuator rams. The instrumentation 110 may be any suitable instrumentation for measuring or detecting soil criteria 200, such as light detection and ranging (LiDar), spectrophotometer, camera, time-of-flight camera, ground-penetrating radar, sonar, x-ray, optical height, electrical conductivity, and electromagnetic induction.

The soil criteria 200 that is monitored or measured may include soil surface residue criteria 200-1, such as the percentage of soil covered by crop residue. The instrumentation 110 used to monitor or measure the surface residue criteria 200-1 may include cameras, infrared sensors or ground-penetrating radar (GPR), such as such as any of the following commercially available systems: (1) the StructureScan™ Mini HR available from GSSI in Nashua, N.H.; (2) the 3d-Radar GeoScope™ Mk IV coupled to a 3d-Radar VX-Series and/or DX-Series multi-channel antenna, all available from 3d-Radar AS in Trondheim, Norway; or (3) the MALA Imaging Radar Array System available from MALA Geoscience in *Mala*, Sweden. Commercially available software such as GPR-SLICE (e.g., version 7.0) available from GeoHiRes International Ltd. in Borken, Germany may be used to generate the signal outputs from the GPR sensor. Thus, the instrumentation 110 would measure the percentage of surface residue at each location in the field, thereby mapping surface residue throughout the field.

Figure 5A:
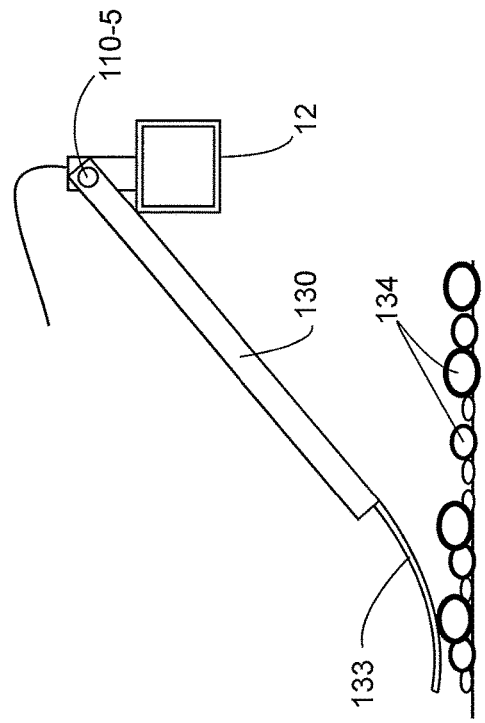
FIG. 5A is an illustration of an embodiment of a sensing arm for detecting soil clod size criteria.
Figure 5B:
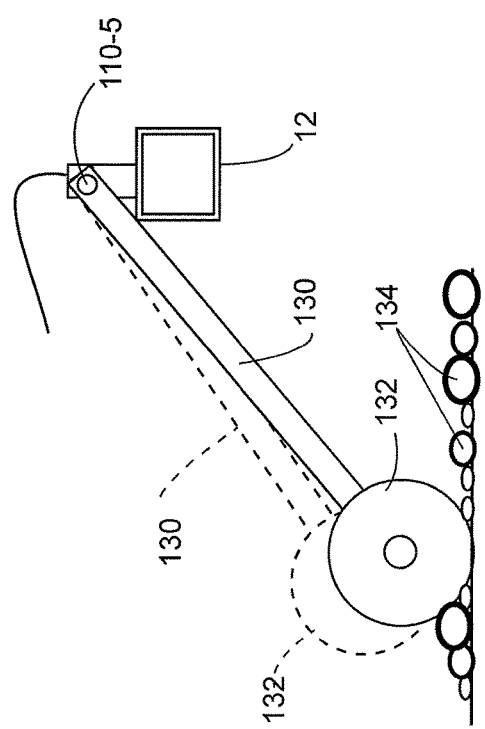
FIG. 5B is an illustration of another embodiment of a sensing arm for detecting soil clod size criteria.
Figure 8:
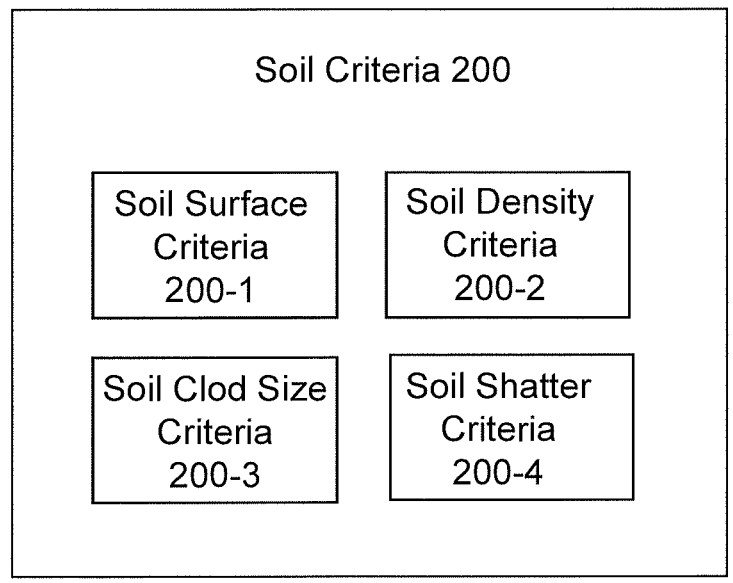
FIG. 8 is a chart identifying types of soil criteria that may be measured or detected.

Another soil criteria 200 that is monitored or measured may include soil clod size criteria 200-3. The instrumentation 110 used to monitor or measure soil clod size criteria 200-3 may include a surface scanner, such as a light detection and ranging (LiDar) system disposed to scan the surface of the soil behind the tillage implement 10. Other instrumentation 110 used to monitor or measure the soil clod size criteria 200-3 may include an optical height sensor disposed to detect the varying heights of clods relative to a predetermined elevation thereby indicating the size of soil clods based on the varying distances. Other instrumentation 110 can be a spectrophotometer, camera, time-of-flight camera, ground-penetrating radar, sonar, x-ray, electrical conductivity, and electromagnetic induction. Other instrumentation 110 used to monitor or measure the soil clod size criteria 200-3 may include an arm 130 with a wheel 132 which rides over the soil surface as shown in FIG. 5A. Alternatively, a resilient horizontal member 133, such as a ski or seed firmer, could replace wheel 132 as shown in FIG. 5B. A rotation sensor or angular deflection sensor 110-5 disposed on the arm or at a pivot point of the arm 130 indicates the size of soil clods 134 based on the rotation or angular deflection of the arm 130. Instead of a rotation sensor, a pressure sensor or other suitable sensors may be used to detect the angular deflection of the arm 130.

Figure 4:
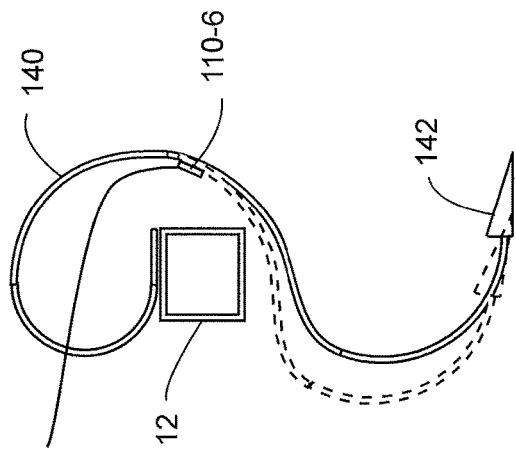
FIG. 4 is an illustration of an embodiment of a shank tillage tool instrumented for detecting soil shatter criteria.
Figure 6:
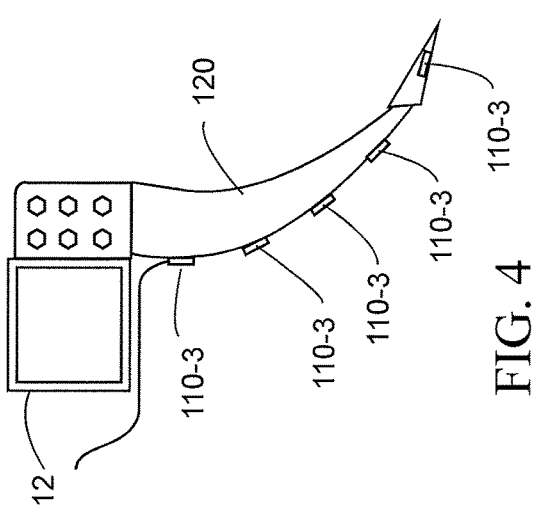
FIG. 6 is an illustration of an embodiment of a an S-tine tillage tool instrumented for detecting soil shatter criteria.

Another soil criteria 200 that is monitored or measured may include soil shatter criteria 200-4 indicative of the extent to which compaction layers are broken up. The instrumentation 110 used to monitor or measure soil shatter criteria 200-4 may include strain gauges 110-3 mounted along the length of one or more shanks as illustrated in FIG. 4 and as discussed above. As shown in FIG. 6, other instrumentation 110 used to monitor or measure soil shatter criteria 200-4 may include a strain gauge or a deflection sensor 110-6 on a resilient arm 140, such as an S-tine on a field cultivator supporting a sweep or point 142, whereby as the resilient arm 140 bends backward during operation, the amount of backward bend or deflection measured by the deflection sensor 110-6 is correlated to the amount of soil compaction.

Figure 7:
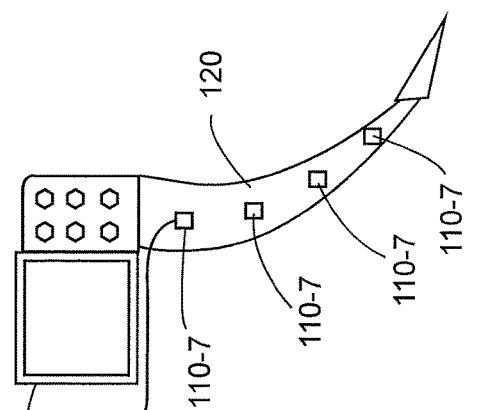
FIG. 7 is an illustration of another embodiment of a shank tillage tool with an electrical conductivity instrument.

Other instrumentation 110 used to monitor or measure soil shatter criteria 200-4 may include x-ray, sonar, ground-penetrating radar, electromagnetic induction and/or electrical conductivity. Electrical conductivity measurement may be made on or between neighboring shanks (or other tillage tools), with the electrical conductivity correlated to a level of soil shatter. For example, lower conductivity is correlated with greater soil shatter, which corresponds to less soil compaction. An embodiment of a shank 120 instrumented with electrical conductivity sensors 110-7 is shown in FIG. 7. By positioning the electrical conductivity sensors 110-7 at different locations along the shank 120, electrical conductivity at varying depths may be identified based on the electrical conductivity output along the length of the shank. As the tillage implement 10 passes through the field, the electrical conductivity at different locations across the field will result in a depth versus electrical conductivity profile of the soil for generating a soil electrical conductivity map of the field.

Another soil criteria 200 that is monitored or measured may include soil density criteria 200-2 based on spatial soil density changes or based on the depth location of soil density changes or based on the magnitude of soil density changes. The instrumentation 110 used to monitor or measure soil density criteria 200-2 based on spatial density changes may include GPR or strain gauges 110-3 mounted to the tillage tools 20 of the tillage implement 10 as discussed in more detail below. Alternatively, as shown in FIG. 3, a load cell 110-4 may be incorporated into the drawbar hitch pin. Similarly, to monitor or measure soil density criteria 200-2 based on depth location of soil density changes or magnitude of soil density changes, the instrumentation may include GPR, a potentiometer, or strain gauges 110-3 positioned at different points along the tillage tool 20 or an arm supporting the tillage tool with the strain gauges correlated to soil density. For example, as shown in FIG. 4, an embodiment of a shank 120 is shown with strain gauges 110-3 positioned at different locations along the shank 120. By positioning the strain gauges 110-3 at different locations along the shank 120, soil compaction layers at varying depths may be identified based on strain gauge output along the length of the shank thereby measuring the depth and/or magnitude of the soil density changes across the field. As the tillage implement 20 passes through the field, the strain measured by the strain gauges at different locations across the field will result in a depth-versus-strain profile of the soil for generating a soil density map of the field.

Tillage Implement Control

Each of the height adjustment actuators 30, depth adjustment actuators 40, angular adjustment actuators 50, and downforce adjustment actuators 60 may be manually actuated by the operator based on the soil criteria 200 displayed to the operator on the display 112. Alternatively, height adjustment actuators 30, depth adjustment actuators 40 and angular adjustment actuators 50, and downforce adjustment actuators 60 may be responsive to output signals generated by the soil monitoring system 100 when the soil monitoring system detects that the soil criteria 200 is outside a desired range.

Surface Residue Control

When the soil monitoring system 100 detects or otherwise displays to the operator that the percentage of soil covered by crop residue soil (i.e., surface residue criteria 200-1) is above a predetermined percentage, the angular adjustment actuators 50 may be actuated to adjust of the disc gang or other tillage tools supported by a subframe 42 to more aggressively chop the residue and throw the soil to reduce the amount of surface residue. The angular adjustment actuators 50 may be manually actuated by the operator from the cab of the tractor based on a notification displayed to the operator on the display monitor 112 in response to signals received by the by the instrumentation 110, e.g. cameras, infrared sensors, GPR, detecting surface residue criteria 200-1. Alternatively the angular adjustment actuators 50 may be automatically actuated based on a signal generated by the display monitor 112 in response to signals received by the by the instrumentation 110 detecting surface residue criteria 200-1. Alternatively, or additionally, the height adjustment actuator 30 may be manually or automatically adjusted as identified above to lower the entire main frame 12 with respect to the ground elevation to increase the depth of penetration of the tillage tools 20 into the soil. Additionally, or alternatively, depth adjustment actuators 40 or downforce actuators 60 coupled to individual the individual subframes 42 supporting disc gangs, rolling basket harrows or other tillage tools may be manually or automatically adjusted as identified above to lower the subframes 42 with respect to the main frame 12 to increase the depth of penetration into the soil or downforce of the tillage tools 20 supported by the subframes.

Clod Size Control

When the soil monitoring system 100 detects or otherwise displays to the operator that soil clod size criteria 200-3 are too large, the soil monitoring system 100 may be programmed to display to the operator on the display monitor 112 an instruction for the operator to adjust the speed of travel. Additionally, or alternatively, the height adjustment actuator 30 may be actuated to increase the down pressure to force the entire main frame 12 lower with respect to the ground elevation to increase the depth of penetration of the tillage tools 20 into the soil. The height adjustment actuators 30 may be manually actuated by the operator from the cab of the tractor based on a notification displayed to the operator on the display monitor 112 in in response to signals received by the by the instrumentation 110, e.g., LiDar, optical height sensors, or arm rotation sensors or angular deflection sensors 110-5 (FIG. 5), detecting the soil clod size criteria 200-3. Alternatively the height adjustment actuators 30 may be automatically actuated based on a signal generated by the display monitor 112 in response to signals received by the by the instrumentation 110, e.g., LiDar, optical height sensors, or arm rotation sensor or angular deflection sensor 110-5 (FIG. 5), detecting soil clod size criteria 200-3. Additionally, or alternatively, depth adjustment actuators 40 or downforce actuators 60 coupled to the individual subframes 42 supporting disc gangs, rolling basket harrows, or other tillage tools may be manually or automatically adjusted as described above to force the subframes 42 downwardly with respect to the main frame 12 to increase the depth of penetration of the tillage tools 20 supported by the subframes into the soil or to increase the pressure applied by the tillage tool 20 to break up soil clods (such as, for example, a rolling basket harrow).

Soil Shatter Control

When the soil monitoring system 100 detects or otherwise displays to the operator that the strain measured by the strain gauges on the shanks and/or deflection measurement of the resilient arm supporting the tillage tool exceeds a predetermined strain or deflection indicative of the soil shatter criteria 200-4, the height adjustment actuator 30 may be actuated to lower the entire main frame 12 with respect to the ground elevation to increase the depth of penetration of the tillage tools 20 into the soil. The height adjustment actuators 30 may be manually actuated by the operator from the cab of the tractor based on a notification displayed to the operator on the display monitor 112 in in response to signals received by the by the instrumentation 110, e.g. strain gauges 110-3 (FIG. 4), or deflection sensors 110-6 (FIG. 6), detecting soil shatter criteria 200-4. Alternatively the height adjustment actuators 30 may be automatically actuated based on a signal generated by the display monitor 112 in response to signals received by the instrumentation 110, e.g. strain gauges 110-3 (FIG. 4), or deflection sensors 110-6 (FIG. 6), detecting soil shatter criteria 200-4. Additionally, or alternatively, depth adjustment actuators 40 or downforce actuators 60 coupled to individual the individual subframes 42 supporting disc gangs, rolling basket harrows, or other tillage tools may be manually or automatically adjusted as described above to lower the subframes 42 with respect to the main frame 12 to increase the depth of penetration into the soil or downforce of the tillage tools 20 supported by the subframes.

Soil Density Control

When the soil monitoring system 100 detects or otherwise displays to the operator that the soil density criteria 200-2 based on spatial soil density changes or based on the depth location of soil density changes or based on the magnitude of soil density changes, the angular adjustment actuators 50 may be actuated to adjust of the disc gang or other tillage tools supported by a subframe 42. The angular adjustment actuators 50 may be manually actuated by the operator from the cab of the tractor based on a notification displayed to the operator on the display monitor 112 in in response to signals received by the by the instrumentation 110, e.g. strain gauges 110-3 (FIG. 4), hitch pin load cell 110-4 (FIG. 3), or deflection sensors 110-6 (FIG. 6), detecting soil density criteria 200-2. Alternatively the angular adjustment actuators 50 may be automatically actuated based on a signal generated by the display monitor 112 in response to signals received by the by the instrumentation 110, e.g. strain gauges 110-3 (FIG. 4), hitch pin load cell 110-4 (FIG. 3), or deflection sensors 110-6 (FIG. 6), detecting soil density criteria 200-2. Alternatively, or additionally, the height adjustment actuator 30 may be manually or automatically adjusted as described above to lower the entire main frame 12 with respect to the ground elevation to increase the depth of penetration of the tillage tools 20 into the soil. Additionally, or alternatively, depth adjustment actuators 40 or downforce actuators 60 coupled to the individual subframes 42 supporting disc gangs, rolling basket harrows, or other tillage tools may be manually or automatically adjusted as described above to lower the subframes 42 with respect to the main frame 12 to increase the depth of penetration into the soil or downforce of the tillage tools 20 supported by the subframes.

Control of Other Implements

In addition to adjusting the tillage implement during tillage operations, the soil criteria 200 gathered during tillage operations may be used to control other implements during subsequent passes over the soil, such as during planting operations. For example, the map of the soil criteria produced by the soil monitoring system 100 during tillage operations may be uploaded or otherwise communicated or interfaced with the planter monitor such that during planting operations adjustments can be made to the planter manually by the operator or automatically.

For example, during planting operations, as the planter is entering a portion of the field where the surface residue criteria 200-1 identified on the soil criteria map exceeds a certain percentage, the row cleaner actuator on the planter may be adjusted manually by the operator from the cab of the tractor (based on a notification displayed to the operator on the planter monitor and/or the display monitor) or the row cleaner actuator may be automatically adjusted based on a signal generated by the planter monitor and/or display monitor 112 interfacing with the soil criteria map to increase the downforce on the row cleaner actuator. A planter having a row cleaner actuator for increasing and decreasing downpressure is disclosed in U.S. Pat. No. 8,763,713, incorporated herein by reference.

As another example, during planting operations, as the planter is entering a portion of the field where the soil density criteria 200-2 identified on the soil criteria map is above a certain threshold, a downforce actuator disposed on the planter may be adjusted manually by the operator from the cab of the tractor (based on a notification displayed to the operator on the planter monitor and/or display monitor 112) or the planter downforce actuator may be automatically adjusted based on a signal generated by the planter monitor interfacing with the soil criteria map to increase the downforce on the planter to ensure proper furrow depth as the planter passes over areas of the field with higher soil densities. A planter equipped with a downforce actuator is disclosed in Publication No. US2014/0026748, incorporated herein by reference. Additionally, or alternatively, as the planter is entering a portion of the field where the soil density criteria 200-2 identified on the soil criteria map is above a certain threshold, the planter's closing wheel downforce actuator may be adjusted manually by the operator from the cab of the tractor (based on a notification displayed to the operator) or the planter closing wheel downforce actuator may be automatically adjusted based on a signal generated by the planter monitor interfacing with the soil criteria map to increase the downforce on the on the closing wheel to ensure proper soil coverage and compaction of the soil over the planted seed. A planter equipped with a closing wheel downforce actuator is disclosed in U.S. Pat. No. 8,544,398, incorporated herein by reference.

Various embodiments of the invention have been described above for purposes of illustrating the details thereof and to enable one of ordinary skill in the art to make and use the invention. The details and features of the disclosed embodiments are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A tillage implement, comprising:
   a frame operably supporting tillage tools; and
   a soil monitoring system comprising instrumentation operably supported from the frame and disposed to detect soil criteria after soil is tilled by the tillage tools, wherein the soil criteria detected is at least one of soil clod size criteria and soil shatter criteria.

2. The tillage implement of claim 1, further comprising: at least one height adjustment actuator for raising and lowering the main frame with respect to a soil surface for adjusting depth of penetration of the tillage tools into the soil surface, and wherein the at least one actuator is adjusted in response to the detected soil criteria.

3. The tillage implement of claim 1, wherein the soil monitoring system further comprises additional instrumentation operably supported from the frame forward of the tillage tools and disposed to detect soil criteria prior to the soil being tilled by the tillage tools.

4. The tillage implement of claim 1, wherein the soil criteria detected is soil clod size criteria.

5. The tillage implement of claim 2, wherein the soil criteria detected is soil clod size criteria.

6. The tillage implement of claim 3, wherein the soil criteria detected is soil clod size criteria.

7. The tillage implement of claim 1, wherein the instrumentation is at least one instrument chosen from LIDAR, spectrophotometer, camera, time of flight camera, ground penetrating radar, sonar, x-ray, optical height, electrical conductivity, and electromagnetic induction.

8. The tillage implement of claim 3, wherein the additional instrumentation is at least one instrument chosen from LIDAR, spectrophotometer, camera, time of flight camera, ground penetrating radar, sonar, x-ray, optical height, electrical conductivity, and electromagnetic induction.

9. The tillage implement of claim 4, wherein the instrumentation comprises a rotation sensor or angular deflection sensor connected through an arm to a wheel or resilient member that engages the soil surface.

10. The tillage implement of claim 1, wherein the instrumentation is at least one of x-ray, sonar, ground-penetrating radar, electrical conductivity, and electromagnetic induction.

11. The tillage implement of claim 3, wherein the additional instrumentation is at least one of x-ray, sonar, ground-penetrating radar, electrical conductivity, and electromagnetic induction.

12. The tillage implement of claim 10, wherein the instrumentation is x-ray.

13. The tillage implement of claim 10, wherein the instrumentation is sonar.

14. The tillage implement of claim 10, wherein the instrumentation is ground-penetrating radar.

15. The tillage implement of claim 10, wherein the instrumentation is electrical conductivity.

16. The tillage implement of claim 10, wherein the instrumentation is electromagnetic induction.

17. The tillage implement of claim 15, wherein the electrical conductivity instrumentation is disposed on the tillage tool.

18. The tillage implement of claim 11, wherein the additional instrumentation is x-ray.

19. The tillage implement of claim 11, wherein the additional instrumentation is sonar.

20. The tillage implement of claim 11, wherein the additional instrumentation is ground-penetrating radar.

21. The tillage implement of claim 11, wherein the additional instrumentation is electrical conductivity.

22. The tillage implement of claim 11, wherein the additional instrumentation is electromagnetic induction.

23. The tillage implement of claim 21, wherein the electrical conductivity instrumentation is disposed on the tillage tool.

24. The tillage implement of claim 1, wherein the soil criteria detected is soil shatter depth criteria, wherein the instrumentation comprises a deflection sensor disposed on a resilient arm mounted to the frame, and wherein the resilient arm is configured to engage the soil.

25. The tillage implement of claim 3, wherein the soil criteria detected is soil shatter depth criteria, wherein the additional instrumentation comprises a deflection sensor disposed on a resilient arm mounted to the frame, and wherein the resilient arm is configured to engage the soil.

26. The tillage implement of claim 1, wherein the soil criteria detected is soil shatter depth criteria, wherein the instrumentation comprises a plurality of strain gauges disposed vertically on a resilient arm mounted to the frame, and wherein the resilient arm is configured to engage the soil.

27. The tillage implement of claim 3, wherein the soil criteria detected is soil shatter depth criteria, wherein the additional instrumentation comprises a plurality of strain gauges disposed vertically on a resilient arm mounted to the frame, and wherein the resilient arm is configured to engage the soil.

28. The tillage implement of claim 26, wherein the strain gauges are disposed on a back side of the resilient arm in a direction of travel of the tillage implement.

29. The tillage implement of claim 27, wherein the strain gauges are disposed on a back side of the resilient arm in a direction of travel of the tillage implement.

30. The tillage implement of claim 1, wherein the soil monitoring system includes a display monitor configured to visually display the detected soil criteria to an operator.

31. The tillage implement of claim 1, further comprising:
a tillage tool depth adjustment actuator configured to raise and lower at least some of the tillage tools independently relative to the frame.

32. The tillage implement of claim 1, further comprising:
an angular adjustment actuator configured to angularly adjust at least some of the tillage tools with respect to the frame and a direction of travel.

33. The tillage implement of claim 1, further comprising:
a downforce actuator configured to increase or decrease a downforce of at least some of the tillage tools independently relative to the frame.

34. The tillage implement of claim 1, wherein the soil monitoring system is configured to communicate with a GPS unit, and wherein the soil monitoring system is configured to map the soil shatter criteria to GPS coordinates.

35. A method of controlling a planter based on soil criteria, the method comprising:
tilling soil of an agricultural field using a tillage implement having a frame operably supporting tillage tools and a soil monitoring system comprising instrumentation operably supported from the frame;
detecting soil criteria after the soil is tilled by the tillage tools using the soil monitoring system, the soil criteria selected from the group consisting of soil clod size criteria and soil shatter criteria;
mapping the soil criteria to GPS coordinates;
adjusting operation of a planter based on the mapped soil criteria.

36. The method of claim 35, wherein detecting soil criteria comprises measuring at least one selected from the group consisting of x-ray, sonar, ground-penetrating radar, electrical conductivity, and electromagnetic induction.

37. The method of claim 35, wherein detecting soil criteria comprises measuring strain using a plurality of strain gauges disposed vertically on a resilient arm mounted to the frame, and wherein the resilient arm engages the soil.

* * * * *